United States Patent [19]

Jones et al.

[11] Patent Number: 4,567,307

[45] Date of Patent: * Jan. 28, 1986

[54] TWO-STEP METHANE CONVERSION PROCESS

[75] Inventors: C. Andrew Jones, Newtown Square; John J. Leonard, Springfield; John A. Sofranko, Malvern, all of Pa.

[73] Assignee: Atlantic Richfield Company, Los Angeles, Calif.

[ * ] Notice: The portion of the term of this patent subsequent to Apr. 17, 2001 has been disclaimed.

[21] Appl. No.: 600,657

[22] Filed: Apr. 16, 1984

Related U.S. Application Data

[63] Continuation-in-part of Ser. No. 522,925, Aug. 12, 1983, Pat. No. 4,443,649, and a continuation-in-part of Ser. No. 522,944, Aug. 12, 1983, Pat. No. 4,444,984, and a continuation-in-part of Ser. No. 522,942, Aug. 12, 1983, Pat. No. 4,443,648, and a continuation-in-part of Ser. No. 522,905, Aug. 12, 1983, Pat. No. 4,443,645, and a continuation-in-part of Ser. No. 522,877, Aug. 12, 1983, Pat. No. 4,443,647, and a continuation-in-part of Ser. No. 522,876, Aug. 12, 1983, Pat. No. 4,443,644, and a continuation-in-part of Ser. No. 522,906, Aug. 12, 1983, Pat. No. 4,443,646, and a continuation-in-part of Ser. No. 522,935, Aug. 12, 1983, and a continuation-in-part of Ser. No. 522,938, Aug. 12, 1983, said Ser. No. 522,925, is a continuation-in-part of Ser. No. 412,667, Aug. 30, 1982, abandoned, said Ser. No. 522,944, is a continuation-in-part of Ser. No. 412,655, Aug. 30, 1982, abandoned, said Ser. No. 522,942, is a continuation-in-part of Ser. No. 412,662, Aug. 30, 1982, abandoned, said Ser. No. 522,905, is a continuation-in-part of Ser. No. 412,663, Aug. 30, 1982, abandoned, said Ser. No. 522,877, is a continuation-in-part of Ser. No. 412,664, Aug. 30, 1982, abandoned, said Ser. No. 522,876, is a continuation-in-part of Ser. No. 412,665, Aug. 30, 1982, abandoned, said Ser. No. 522,906, is a continuation-in-part of Ser. No. 412,666, Aug. 30, 1982, abandoned, said Ser. No. 522,935, is a continuation-in-part of Ser. No. 412,649, Aug. 30, 1982, abandoned, said Ser. No. 522,938, is a continuation-in-part of Ser. No. 412,650, Aug. 30, 1982, abandoned.

[51] Int. Cl.$^4$ .......................... C07C 2/02; C07C 5/00
[52] U.S. Cl. .................................. 585/330; 585/500; 585/525; 585/533; 585/943
[58] Field of Search ............... 585/330, 525, 533, 500, 585/943

[56] References Cited

U.S. PATENT DOCUMENTS

| | | | |
|---|---|---|---|
| 4,450,311 | 5/1984 | Wright et al. | 585/413 |
| 4,451,685 | 5/1984 | Neuitt et al. | 585/525 |

OTHER PUBLICATIONS

Fang et al, J. Chinese Chem. Soc. (1981) pp. 265–273.

*Primary Examiner*—Curtis R. Davis
*Attorney, Agent, or Firm*—Craig E. Larson

[57] ABSTRACT

A method of synthesizing hydrocarbons from a methane source which includes the steps of contacting a methane with an oxide of a metal which oxide when contacted with methane at between about 500° and 1000° C. is reduced and produces higher hydrocarbon products and water, recovering ethylene from the effluent of the contacting and oligomerizing the ethylene to produce higher hydrocarbon products.

15 Claims, No Drawings

4,567,307

TWO-STEP METHANE CONVERSION PROCESS

CROSS REFERENCES TO RELATED APPLICATIONS

This application is a continuation-in-part of the following U.S. patent applications: (1) application Ser. No. 522,925 filed Aug. 12, 1983 now U.S. Pat. No. 4,443,649, which in turn is a continuation-in-part of application Ser. No. 412,667 filed Aug. 30, 1982, now abandoned; (2) application Ser. No. 522,944 filed Aug. 12, 1983, now U.S. Pat. No. 4,444,984, which in turn is a continuation-in-part of application Ser. No. 412,655 filed Aug. 30, 1982, now abandoned; (3) application Ser. No. 522,942 filed Aug. 12, 1983, now U.S. Pat. No. 4,443,648, which in turn is a continuation-in-part of application Ser. No. 412,662 filed Aug. 30, 1982, now abandoned; (4) application Ser. No. 522,905 filed Aug. 12, 1983, now U.S. Pat. No. 4,443,645, which in turn is a continuation-in-part of application Ser. No. 412,663 filed Aug. 30, 1982, now abandoned; (5) application Ser. No. 522,877 filed Aug. 12, 1983, now U.S. Pat. No. 4,443,647, which in turn is a continuation-in-part of application Ser. No. 412,664 filed Aug. 30, 1982, now abandoned; (6) application Ser. No. 522,876 filed Aug. 12, 1983, now U.S. Pat. No. 4,443,644, which in turn is a continuation-in-part of application Ser. No. 412,665 filed Aug. 30, 1982, now abandoned; (7) application Ser. No. 522,906 filed Aug. 12, 1983, now U.S. Pat. No. 4,443,646, which in turn is a continuation-in-part of application Ser. No. 412,666 filed Aug. 30, 1982, now abandoned; (8) application Ser. No. 522,935 filed Aug. 12, 1983, which in turn is a continuation-in-part of application Ser. No. 412,649 filed Aug. 30, 1982, now abandoned; and (9) application Ser. No. 522,938 filed Aug. 12, 1983, which in turn is a continuation-in-part of application Ser. No. 412,650 filed Aug. 30, 1982, now abandoned. The entire content of these applications is incorporated herein by reference.

BACKGROUND OF THE INVENTION

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_{3}+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products.

Recently, it has been discovered that methane may be converted to higher hydrocarbons by a process which comprises contacting methane and an oxidative synthesizing agent at synthesizing conditions (e.g., at a temperature selected within the range from about 500° to about 1000° C.). Oxidative synthesizing agents are compositions having as a principal component at least one oxide of at least one metal which compositions produce $C_2+$ hydrocarbon products, co-product water, and a composition comprising a reduced metal oxide when contacted with methane at synthesizing conditions. Reducible oxides of several metals have been identified which are capable of converting methane to higher hydrocarbons. Oxides of manganese, tin, indium, germanium, lead, antimony and bismuth are particularly useful. See commonly-assigned U.S. patent application Ser. No. 522,925, now U.S. Pat. No. 4,443,649; Ser. No. 522,944, now U.S. Pat. No. 4,444,984; Ser. No. 522,942, now U.S. Pat. No. 4,443,648; Ser. No. 522,905, now U.S. Pat. No. 4,443,645; Ser. No. 522,877, now U.S. Pat. No. 4,443,647; Ser. No. 522,876, now U.S. Pat. No. 4,443,644; and Ser. No. 522,906, now U.S. Pat. No. 4,443,646; all filed Aug. 12, 1983.

Commonly-assigned U.S. patent application Ser. No. 522,935, filed Aug. 12, 1983, discloses and claims a process which comprises contacting methane with an oxidative synthesizing agent under under elevated pressure (e.g., 2-100 atmospheres) to produce greater amounts of $C_3+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

Commonly-assigned U.S. patent application Ser. No. 522,937, filed Aug. 12, 1983, now U.S. Pat. No. 4,499,322 discloses and claims a process for the conversion of methane to higher hydrocarbons which comprises contacting methane with an oxidative synthesizing agent containing a promoting amount of alkali metal and/or compounds thereof. The entire content of this application is incorporated herein by reference.

Commonly-assigned U.S. patent application Ser. No. 522,936 filed Aug. 12, 1983, now U.S. Pat. No. 4,499,936 discloses and claims a process for the conversion of methane to higher hydrocarbons which comprises contacting methane with an oxidative synthesizing agent containing a promoting amount of alkaline earth metal and/or compounds thereof. The entire content of this application is incorporated herein by reference.

Commonly-assigned U.S. patent application Ser. No. 06/600,665, now U.S. Pat. No. 4,499,323 discloses and claims a process for the conversion of methane to higher hydrocarbons which comprises contacting methane with a contact solid comprising a reducible oxide of praseodymium and at least one member of the group consisting of alkali metals, alkaline earth metals, and compounds thereof. The entire content of this application is incorporated herein by reference.

Commonly-assigned U.S. patent application Ser. No. 06/600,918, discloses and claims a process for the conversion of methane to higher hydrocarbons which comprises contacting methane with a contact solid comprising a reducible oxide of terbium and at least one member of the group consisting of alkali metals, alkaline earth metals, and compounds thereof. The entire content of this application is incorporated herein by reference.

Commonly-assigned U.S. patent application Ser. No. 06/600,917, now U.S. Pat. No. 4,499,324 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof. The entire content of this application is incorporated herein by reference.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. The entire content of this application is incorporated herein by reference.

Commonly-assigned U.S. patent application Ser. No. 06/600,669, now U.S. Pat. No. 4,489,215 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof.

The reaction products of such processes are mainly ethylene, ethane, other light hydrocarbons, carbon oxides, coke and water.

The main object of the present invention is a multistage process for converting a gas comprising methane to higher hydrocarbon, preferably normally liquid hydrocarbons, and more preferably aliphatic hydrocarbons within the gasoline boiling range.

SUMMARY OF THE INVENTION

According to one embodiment of the present invention, hydrocarbon products are produced from a gas comprising methane by: (1) contacting a gas comprising methane and at least one reducible oxide of at least one metal at temperature conditions to reduce such reducible oxide and produce higher hydrocarbon products and water; and (2) oligomerizing at least a portion of such higher hydrocarbon products at reduced temperature conditions relative to step (1) to produce still higher hydrocarbon products, preferably normally liquid hydrocarbon products.

According to another embodiment of the present invention, normally liquid hydrocarbons are produced from a gas comprising methane by: (1) contacting at a temperature selected within the range of about 500° to 1000° C. a gas comprising methane and at least one reducible oxide of at least one metal which oxides when contacted with methane at said temperature are reduced and produce higher hydrocarbon products and water; (2) recovering a gas comprising ethylene from the effluent of said contacting and (3) oligomerizing said ethylene to produce normally liquid hydrocarbon products.

DETAILED DESCRIPTION OF THE INVENTION

In addition to methane the feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The solid which is contacted with methane in the first stage of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof. Alkali and alkaline earth metals and compounds have been found to improve the hydrocarbon product selectivity of these agents. The further incorporation of phosphorus into agents promoted by alkali or alkaline earth components enhances catalyst stability.

Reducible oxides of cerium, praseodymium, and terbium have also been found to be effective for the conversion of methane to higher hydrocarbons, particularly when the rare earth component is associated with an alkali or alkaline earth metal component.

Reducible oxides of iron and ruthenium have also been found to be effective for the conversion of methane to higher hydrocarbons, particularly when associated with an alkali or alkaline earth metal component.

The metal components may be associated with other support materials such as silica, magnesia, alumina, titania, zirconia and the like and combinations thereof. When employing agents containing rare earth components—oxides of Ce, Pr and Tb—the rare earth oxides preferably serve as supports.

Reducible oxides of manganese have been found to be particularly desirable for methane conversion, especially when associated with an alkali metal (preferably sodium). Especially preferred agents comprise silica- and/or magnesia-supported agents containing oxides of manganese and sodium.

The solid contacted with methane in the first step of the present invention can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkaline or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solids calcined, preferably in air, at a temperature within the range of about 300° to 1200° C. Particular calcination temperatures will vary depending upon the particular metal compound or compounds employed.

Regardless of how the components of the agent are combined, the composite will be dried and calcined at elevated temperatures in an oxygen-containing gas (e.g., air) prior to use of the process of this invention.

Preferably, methane is contacted with the agent in the substantial absence of catalytically effective nickel, noble metals and compounds thereof (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the first step of this invention relative to such contacting in the absence of such metals and compounds thereof.

Operating temperatures for the first step of the method of this invention are generally within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 30 atmospheres.

Contacting methane and a reducible metal oxide to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

In carrying out the first step of the present process, a single reactor apparatus containing a fixed bed of solids may be used with intermittent or pulsed flow of a first gas comprising methane and a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising at least one reducible oxide of at least one metal to form higher hydrocarbon products, co-product water, and reduced metal oxide; (b) removing particles comprising reduced metal oxide from the first zone and contacting the reduced particles in a second zone with an oxygen-containing gas to form particles comprising a reducible metal oxide; and (c) returning the particles produced in the second zone to the first zone. The steps are preferably repeated at least periodically, and more preferably the steps are continuous. In the more preferred embodiment solids are continuously circulated between at least one methane-contact zone and at least one oxygen-contact zone.

Particles comprising a reducible metal oxide which are contacted with methane may be maintained as fluidized, ebullating, or entrained beds of solids. Preferably methane is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In the more preferred embodiment of the present invention, methane feedstock and particles comprising a promoted oxidative synthesizing agent are continuously introduced into a methane contact zone maintained at synthesizing conditions. Synthesizing conditions include the temperatures and pressures described above. Gaseous reaction products from the methane contact zone (separated from entrained solids) may be further processed—e.g., they may be passed through a fractionating system wherein the desired hydrocarbon products are separated from unconverted methane and combustion products. Unconverted methane may be recovered and recycled to the methane contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the methane contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material deposited on the particles. At least a portion of the particles comprising promoted oxidative synthesizing agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of the synthesizing system.

The effluent produced by the first stage of the method of this invention comprises unconverted methane and higher hydrocarbons as well as carbon oxides and water. It is within the scope of the present invention to recover a portion of the first stage effluent (e.g., unconverted methane) for recycle to the methane contact zone. Similarly, carbon oxides and water may be removed from the first stage effluent prior to further treatment of the effluent in accordance with the present invention.

Whether or not such intermediate separations are employed, a higher hydrocarbon stream containing olefins is produced in the first stage and all or a portion of such stream is passed to the second stage of the process of this invention wherein still higher hydrocarbon products are produced by oligomerization.

Numerous catalysts and processes are known for the oligomerization of olefins generally, and of ethylene particularly. For example, phosphoric acid supported on a kieselguhr base has been widely used for making polymer gasoline (i.e., olefinic hydrocarbon liquids within the gasoline boiling range) from refinery gases. Other catalysts which have been employed for similar purposes include the oxides of cobalt, nickel, chromium, molybdenum and tungsten on supports such as alumina, silica-alumina, kieselguhr, carbon and the like.

Included within the broad scope of the present invention are all catalysts and processes which are effective for the oligomerization of olefins to higher hydrocarbons, preferably olefinic hydrocarbon liquids within the gasoline boiling range. Without intending to limit the scope of the claimed invention, most oligomerization catalysts may be classified in one of two general categories: metal catalysts and acid catalysts. They may also be classified as heterogeneous (solid) catalysts or homogeneous (liquid-phase) catalysts.

For examples of metal catalysts based on nickel, see U.S. Pat. Nos. 2,828,347; 3,459,826; 3,527,839; 3,954,668; 3,959,400; 4,260,844; 4,272,406; 4,288,648; 4,293,725; and *Industrial Chemistry*, 47 pp. 752, et seq. (1955). Note that these catalysts require a donor ligand and a Lewis acid. For examples of metal catalysts based on palladium, see U.S. Pat. Nos. 3,644,565; 3,728,415; 3,738,977; 3,758,626; and 3,920,763. An example of metal catalysts based on chromium is found in U.S. Pat. No. 3,709,954. An example of metal catalysts based on cobalt is found in *Industrial and Engineering Chemistry*, 42, pp. 2580, et seq. (1950). Examples of metal catalysts based on titanium on found in U.S. Pat. Nos. 3,981,941 and 4,110,410. An example of metal catalysts based on tungsten is found in U.S. Pat. No. 3,903,193. An example of metal catalysts based on rheminum is found in U.S. Pat. No. 3,393,251.

Examples of phosphoric acid catalyst are described in U.S. Pat. Nos. 2,383,318 and 3,887,634 and also in *Industrial and Engineering Chemistry*, 27, pp. 1364, et seq. (1935). Acid catalysts based on chlorided or fluorided alumina are found in U.S. Pat. Nos. 3,364,191 and 3,515,769 and also in USSR Pat. No. 107,176.

Other acid catalysts of particular interest in the context of the present invention are silaceous, crystalline molecular sieves. Such silica-containing crystalline materials include materials which contain, in addition to silica, significant amounts of alumina. These crystalline materials are frequently named "zeolites", i.e., crystalline aluminosilicates. Silica-containing crystalline materials also include essentially aluminum-free silicates. These crystalline materials are exemplified by crystalline silica polymorphs (e.g., silicalite, disclosed in U.S. Pat. No. 4,061,724 and organosilicates, disclosed in U.S. Pat. No. Re. 29948), chromia silicates (e.g., CZM), ferrosilicates and galliosilicates (see U.S. Pat. No. 4,238,318), and borosilicates (see U.S. Pat. Nos. 4,226,420; 4,269,813; and 4,327,236).

Crystalline aluminosilicate zeolites are best exemplified by ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see U.S. Pat. No. 4,016,246). Examples of processes for the conversion of low molecular weight olefins over zeolites are found in U.S. Pat. Nos. 2,972,643; 3,325,465; 3,960,978; 3,972,832; 4,021,502; 4,044,065; 4,150,062; and 4,254,295. Also see U.S. Pat. Nos. 4,417,086 and 4,417,087 wherein oligomerization processes employing fluidized crystalline molecular sieves are disclosed.

Metal oligomerization catalysts in general are more sensitive to feed impurities, (e.g., water, carbon monoxide, dienes, etc.) then are the acid catalysts. Although homogeneous, metal catalysts are quite active, the need for dry feeds, solvents, and other measures to prevent catalyst deactivation and precipitation is disadvantageous and suggests an obvious advantage to supported, heterogeneous, metal catalyst. Homogeneous acid catalysts are effective but are also corrosive and tend to form two liquid-phase systems with the non-polar hydrocarbon oligomerization products. Considering the foregoing observations, heterogeneous acid catalysts are the preferred catalyst for use in the oligomerization step of the present invention. Of the heterogeneous acid catalysts, acid zeolites are especially preferred, particularly zeolites of the ZSM-type and borosilicates.

The oligomerization step of the present invention may be performed according to any of the numerous processes known to those skilled in the art.

What is claimed is:

1. A process for converting methane to higher hydrocarbon products which comprises:
   (a) contacting methane with a first agent at conditions effective to produce higher hydrocarbon products and water, said first agent comprising at least one reducible oxide of at least one metal which oxide when contacted with methane at a temperature in the range of about 500° C. to about 1000° C. is reduced and produces higher hydrocarbon products and water; and
   (b) oligomerizing at least a portion of said higher hydrocarbon product to still higher hydrocarbon products in the presence of an effective amount of a second agent capable of promoting said oligomerization, provided that the composition of said first agent is different from the composition of said second agent.

2. A process for converting methane to higher hydrocarbon products which comprises:
   (a) contacting at a temperature selected within the range of about 500° to 1000° C. a gas comprising methane and at least one reducible oxide of at least one metal which oxides when contacted with methane at said temperature are reduced and produce higher hydrocarbon products and water, said contacting being carried out in the substantial absence of catalytically effective Ni, Rh, Pd, Ag, Os, Ir, Pt, Au and compounds thereof, and said contacting producing an effluent comprising ethylene and (b) oligomerizing said ethylene to produce higher hydrocarbon products.

3. The method of claim 2 wherein the gas comprising methane contains about 40 to 100 vol. % methane.

4. The method of claim 2 wherein the gas comprising methane contains about 80 to 100 vol. % methane.

5. The method of claim 2 wherein the gas comprising methane contains about 90 to 100 vol. % methane.

6. The method of claim 2 wherein the gas comprising methane is derived from natural gas.

7. The method of claim 2 wherein the gas comprising methane is derived from processed natural gas.

8. The method of claim 2 wherein a gas consisting essentially of methane is contacted with the said reducible oxide.

9. The method of claim 2 wherein said reducible metal oxide is associated with a support material.

10. The method of claim 2 wherein said reducible metal oxide is selected from the group consisting of oxides of Mn, Sn, In, Ge, Sb, Pb, Bi and mixtures thereof.

11. The method of claim 2 wherein said reducible metal oxide is an oxide of manganese.

12. The method of claim 2 wherein said ethylene oligomerization is catalyzed by a heterogeneous acid catalyst.

13. The method of claim 12 wherein said catalyst is a siliceous, crystalline molecular sieve.

14. The method of claim 13 wherein said molecular sieve is a ZSM-type zeolite.

15. The method of claim 13 wherein said molecular sieve is a borosilicate.

* * * * *